United States Patent
Lee et al.

(10) Patent No.: US 7,238,343 B2
(45) Date of Patent: *Jul. 3, 2007

(54) COSMETIC METHOD AND COMPOSITION FOR ENHANCING ATTRACTIVENESS

(75) Inventors: Robert Stanley Lee, Wirral (GB); Allan Watkinson, Guisborough (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 529 days.

This patent is subject to a terminal disclaimer.

(21) Appl. No.: 10/733,185

(22) Filed: Dec. 11, 2003

(65) Prior Publication Data

US 2004/0120909 A1   Jun. 24, 2004

(30) Foreign Application Priority Data

Dec. 13, 2002   (GB) ................ 0229071.6

(51) Int. Cl.
*A61Q 15/00*    (2006.01)
*A61K 8/00*     (2006.01)
*A61K 8/02*     (2006.01)

(52) U.S. Cl. ............... 424/65; 424/66; 424/68; 424/400; 424/401

(58) Field of Classification Search ........... 424/65, 424/66, 68, 400, 401
See application file for complete search history.

(56) References Cited

U.S. PATENT DOCUMENTS

| 5,260,053 A | 11/1993 | Chappell et al. ............ 424/65 |
| 5,445,882 A | 8/1995 | Kobayashi et al. ......... 428/329 |
| 6,221,345 B1 | 4/2001 | Esser ............................ 424/65 |
| 6,372,234 B1 | 4/2002 | Deckers et al. ............. 424/401 |
| 6,503,492 B2 * | 1/2003 | McGlone et al. ............ 424/65 |
| 6,713,051 B2 * | 3/2004 | Mayes et al. ................ 424/65 |
| 2006/0115441 A1 * | 6/2006 | James et al. ................. 424/66 |

FOREIGN PATENT DOCUMENTS

| WO | 97/48373 | 12/1997 |
| WO | 02/069924 | 9/2002 |
| WO | 03/000218 | 1/2003 |

OTHER PUBLICATIONS

Co-pending U.S. Appl. No. 10/174,245, filed Jun. 18, 2002, Mayes et al.

* cited by examiner

*Primary Examiner*—Shelley A. Dodson
(74) *Attorney, Agent, or Firm*—Karen E. Klumas

(57) ABSTRACT

Hair removal, especially from armpits damages skin, for example by irritating it, and this can be exacerbated by the application of antiperspirants to control body odour generation. In the present invention, the deleterious effects of hair removal, eg shaving, and antiperspirancy can be ameliorated by employing antiperspirant compositions containing a natural oil and glycerol to a combined concentration of from 1.5 to 15% by weight and in a weight ratio of from 4:1 to 1:4.

30 Claims, No Drawings

COSMETIC METHOD AND COMPOSITION FOR ENHANCING ATTRACTIVENESS

The present invention relates to a cosmetic method and compositions for enhancing attractiveness, and in particular to antiperspirant formulations and to cosmetic methods of controlling perspiration from localised areas of the body, such as from the underarm in conjunction with a method for localised hair removal.

For many years, humans have employed cosmetic methods to prevent or at least ameliorate bodily functions which society at the time under consideration considers to be unsightly or otherwise undesirable. These methods have included controlling the appearance of sweat by topical application of an active which prevents egress of sweat from the eccrine glands, especially in the underarm and also shaving or the use of depilators to remove hair. In the underarm, the first method is commonly employed by both genders, and the second method commonly, though not exclusively, by ladies. Hair removal from the underarm is considered by many ladies in many countries to enhance their appearance, but conventional methods, such as shaving or the use of depilators, irritate the skin and can result in a reduction in skin elasticity and/or a reduction in the moisture content of the stratum corneum. Moreover, conventional antiperspirants can exacerbate irritation, especially if applied to skin from which hair has been removed recently. The application of antiperspirant formulations to skin which had been shaved shortly before can sometimes sting or otherwise be unpleasant for the user. Moreover, the application of antiperspirant can exacerbate the skin damage caused by hair removal. That can manifest itself in the form of irritation and redness and/or also by stinging, when a material such as an antiperspirant composition is applied. Accordingly, underarm beauty and acceptable suppression of odour generation can be achieved at the expense of some pain or at least discomfort to the user.

It is accordingly an object of the present invention to identify antiperspirant formulations which can assist skin to recover better or faster after hair removal or at least ameliorate any pain or discomfort from the beauty and odour treatment regime, or to reduce the impact of subsequent hair removal, whilst simultaneously still controlling or preventing the appearance of sweat and/or generation of odour.

Antiperspirant compositions have been disclosed which contain a moisturising agent such as glycerol, for example in EP 910334A, but in the context of the challenge of hair removal, it would be desirable to find a means to improve upon the use of such a moisturising agent alone.

Cosmetic compositions have been proposed which contain high proportions of fatty acid triglyceride mixtures. For example, a water in oil emulsion containing 25% of a mixture of such triglycerides has been proposed in U.S. Pat. No. 5,445,882, also in the presence of 5% glycerin, but such compositions are considered to be too oily for regular antiperspirant use. Whilst consumers desire their antiperspirants to be smooth on application, many of them do not like them to feel oily. Likewise, U.S. Pat. No. 6,372,234 discloses cosmetic compositions comprising oil bodies. A number of the compositions disclosed also contain glycerin but in only a very small weight ratio to the oil bodies of around 1:20 to 1:100.

In WO03/000218, Unilever discloses in Examples 16.2 and 17.1 and 17.3 compositions containing glycerol, but does not contemplate the presence of selected glyceride oils.

In WO20/069924, Procter & Gamble discloses antiperspirant compositions comprising essentially a vitamin B3 and glycerol, the latter being added to alter the refractive index of the mixture in order to reduce visible deposits. It does not contemplate the use of glyceride carrier oils, though it does contemplate employment of a solid wax, for example that obtained by hydrogenating an oil.

U.S. Pat. No. 5,260,053 discloses deodorant compositions employing glycerol as the main liquid carrier and a very small fraction of coriander oil, but do not contain an antiperspirant active. The presence of such a high proportion of glycerol renders them sticky.

BRIEF SUMMARY OF THE PRESENT INVENTION

According to one aspect of the present invention, there is provided an antiperspirant or deodorant composition suitable for topical application to skin and providing a skin-care benefit which comprises:
a) an antiperspirant active in an amount of from 1 to 50 by weight,
b) a natural oil that comprises a glyceride of an unsaturated carboxylic acid containing 18 carbon atoms
c) glycerol constituents b) and c) being selected in a weight ratio of from 4:1 to 1:4 and together constituting 1.5 to 15% by weight of the composition and:
d) a carrier fluid for the antiperspirant active other than constituents b) and c) or a low molecular weight aliphatic monohydric alcohol in an amount of from 30 to 93% by weight.

By the employment of the glyceride oil in conjunction with glycerol, both of them in low amounts and together amounting to not more than 15% of the composition in the specified ratio range, it is possible to accelerate the recovery of human skin from the unwanted, deleterious side-effects of hair removal or to condition the skin to resist such side effects, whilst at the same time retaining the benefit of controlling sweating. The two constituents contribute in their different ways to overcoming the challenge of repeated hair removal, by together improving the moisturisation of the skin and improving its barrier properties. Moreover, by the employment of limited amounts of both the two constituents in proportions that differ by only a limited extent from weight parity, it is possible to obtain benefit from both constituents whilst mitigating disadvantageous sensory effects that could arise by employing larger amounts of either constituent without the other. Thus, the presence of not too much glycerol mitigates oiliness from glyceride oils and the presence of not too much of the glyceride oils mitigates stickiness from glycerol.

In a second aspect of the present invention, there is provided a cosmetic method for aiding the recovery of human skin from side effects of hair removal whilst controlling perspiration or conditioning the skin to ameliorate such side effect comprising applying topically to the skin a composition comprising:
a) an antiperspirant active in an amount of from 1 to 50% by weight,
b) a natural oil that comprises a glyceride of an unsaturated carboxylic acid containing 18 carbon atoms
c) glycerol constituents b) and c) being selected in a weight ratio of from 4:1 to 1:4 and together constituting 1.5 to 15% by weight of the composition and:
d) a carrier fluid for the antiperspirant active other than constituents b) and c) or a low molecular weight aliphatic monohydric alcohol in an amount of from 30 to 93% by weight before and/or after hair removal from the skin.

DETAILED DESCRIPTION OF THE INVENTION AND PREFERRED EMBODIMENTS

The present invention relates to antiperspirant or deodorant compositions that are suitable for use in conjunction with hair removal from the same area of skin and to cosmetic methods involving both hair removal and perspiration control employing such antiperspirant compositions. Moreover, the proportions and relative proportions of the constituents are selected in order to resist the challenge of hair removal whilst avoiding undesirable sensory negatives that could arise from an excessive proportion on one of the constituents alone.

The antiperspirant active employed herein comprises an astringent aluminium or zirconium salt. The proportion of antiperspirant active present in the composition according to the invention may be from 1–40% by weight of the composition, preferably at least 5% by weight and more preferably 15–30% by weight of a composition not intended for mixture with a propellant, or 15 to 50% in a base composition intended for mixture with a propellant that may be employed in order to make an aerosol composition.

Examples of suitable actives include aluminium salts, zirconium salts, aluminium and/or zirconium complexes, for example aluminium halides, aluminium hydroxy halides, zirconyl oxyhalides, zirconyl hydroxyhalides, and mixtures thereof. However, it is desirable to employ basic aluminium and/or zirconium salts, as such or complexed, suitable complexants including aminoacids, including particularly glycine, and especially salts in which the halide is chloride. Specific examples of preferred salts include activated aluminium chlorohydrate, aluminium chlorohydrate, aluminium pentachlorohydrate and aluminium zirconium chlorohydrate. Useful zirconium salts include zirconium hydroxy-chloride and zirconium oxychloride. Various generally used actives will be known to those skilled in the art. Preferred antiperspirant actives include ZAG (Zirconium Aluminium Glycine), AAZG (Activated Aluminium Zirconium Glycine), and AACH (Activated Aluminium Chorohydrate) activation for example as described in EP6739. In practice, the choice of antiperspirant employed will also take into local regulations, so that in many countries, aerosol formulations employ aluminium salts.

The antiperspirant active can be present in particulate form whereupon it is normally suspended in a suitable carrier fluid, that is to say a carrier fluid in which it is substantially insoluble, which carrier is usually water-immiscible, and which can be structured or thickened. The particle size of the antiperspirant salt is at the discretion of the producer of the composition, though in practice, it will normally comprise particles that are mainly in the diameter range of from 0.1 to 100 µM, and in many instances providing a weight average particle diameter of from 10 to 60 µM. The particle size and distribution will commonly also take into account the applicator in accordance with principles known to the skilled person.

Alternatively the antiperspirant active can be dissolved in a polar carrier, such as for example in aqueous solution or in a polar low weight dihydric alcohol such as propylene glycol and/or dipropylene glycol, advantageously at a concentration of 30 to 60% by weight in such a carrier.

In some embodiments, the antiperspirant active described above is incorporated at a concentration such as from 0.1 to 5% by weight which imparts deodorancy without always meeting national minimum standards for antiperspirancy.

The compositions according to the present invention can also comprise 0.01 to 5% of a deodorant active in addition to any antiperspirant active. The deodorant active used in the cosmetics of the invention can be any deodorant active known in the art such as antimicrobial actives such as polyhexamethylene biguanides, e.g. those available under the trade name Cosmocil™ or chlorinated aromatics, eg triclosan available under the trade name Irgasan™, non-microbiocidal deodorant actives such as triethylcitrate, bactericides and bacteriostatis. Yet other deodorant actives can include zinc salts such as zinc ricinoleate.

The natural oil which is employed herein comprises one or more unsaturated C18 fatty acid glycerides. In many instances, one or more triglycerides are present. The fatty acid residues in the oils can comprise, commonly, from one to three olefinic unsaturated bonds and often one or two. Whilst in many instances the olefinic bonds adopt the trans configuration, in a number of desirable products the bond or bonds adopt the cis configuration. If two or three olefinic unsaturated bonds are present, they can be conjugated. The fatty acid can also be substituted by an hydroxyl group.

The natural oils employable herein desirably comprise one or more triglycerides of oleic acid, linoleic acid, linolenic acid or ricinoleic acid. Various isomers of such acids often have common names, including linolenelaidic acid, trans 7-octadecenoic acid, parinaric acid, pinolenic acid punicic acid, petroselenic acid and stearidonic acid. It is especially desirable to employ glycerides derived from oleic acid, linoleic acid or petroselenic acid, or a mixture containing one or more of them.

Natural oils containing one or more of such triglycerides include coriander seed oil for derivatives of petroselinic acid, impatiens balsimina seed oil, parinarium laurinarium kernel fat or sabastiana brasilinensis seed oil for derivatives of cis-parinaric acid, dehydrated castor seed oil, for derivatives of conjugated linoleic acids, borage seed oil and evening primrose oil for derivatives of linoleic and linolenic acids, aquilegia vulgaris oil for columbinic acid and sunflower oil or safflower oil for derivatives of oleic acid, often together with linoleic acids. Other suitable oils are obtainable from hemp, which can be processed to derive stearadonic acid derivatives and maize corn oil. An especially convenient natural oil by virtue of its characteristics and availability comprises sunflower oil, ranging from those rich in oleic acid glycerides to those rich in linoleic acid glycerides, rich indicating that its content is higher than that of the other named acid.

The proportion of the natural oil in the composition is often selected in the range of from 0.3 to 10% by weight, especially in the range of from at least 0.5% by weight and particularly in the range of up to 6% by weight. In a number of desirable or particularly desirable embodiments of the present invention, the glyceride oil or mixture of oils is employed in a proportion of 0.5%, 1%, 2% or 4% of the total weight of the composition.

A third essential constituent of the composition comprises glycerol. This is often present at a concentration of from 0.5 to 10% by weight of the composition, and particularly from 0.5 to 6% by weight. In a number of desirable or particularly desirable embodiments of the present invention, the glycerol is employed in a proportion of 0.5%, 1%, 2% or 4% of the total weight of the composition. Although the glycerol may be incorporated as a liquid into the composition, at least a fraction of it may alternatively be incorporated as a premixture with the antiperspirant active particles or an alternative receptive particulate material, in effect absorbed or adsorbed within or on the surface of such particles. The weight ratio of the glycerol to suspended antiperspirant active is often in the range of from 1:8 to 1:25. The weight ratio of the glycerol to dissolved antiperspirant active is often in the range of from 1:4 to 1:10.

The combined proportions of the oil and the glycerol in the composition (or base composition for an aerosol) is often chosen in the range of at least 2%. The combined proportions of those two constituents conveniently is up to 10% and in many instances is not greater than 8% of the composition as a whole. It will naturally be recognised that the beneficial effects from the combination tend to be greater or faster observed when a larger rather than a smaller proportion of the two materials is present. Indeed, a particularly desirable ratio of such preferred combined proportions is often from 2:1 to 1:2.

The weight ratio of the glyceride oil to the glycerol is often selected in the range of at least 1:2, and particularly at least 1:1 or in the region of 1:1. In many desirable embodiments the weight ratio of oil to glycerol is not greater than 2:1.

The other carrier liquids (constituent d) to employ for preference depend on the nature of the eventual antiperspirant or deodorant composition which it is desired to make. The formulations can be anhydrous or aqueous, and in the form of a solution, an emulsion or a suspension, as desired.

The total proportion of carrier materials in the instant invention compositions includes both constituents b) and c). The balance (constituent d) of the carrier materials is provided by one or more other liquid materials. Such other carrier liquids can comprise water and/or dihydric alcohols and/or one or more water-immiscible carrier liquids. Where water is employed to provide at least a fraction of the carrier liquid, the formulation will normally comprise an emulsion, which in many instances is an oil in water emulsion. The carrier material can comprise one or more of volatile carrier fluids and/or one or more of non-volatile fluids. The carrier material, or in the case of an emulsion the continuous phase thereof can be structured or thickened by one or a combination of thickener and/or structurant materials if desired that is suitable for the nature of the carrier material. The carrier materials together can often comprise up to about 90 wt %, in many instances up to 70 wt % of the composition, or of the base composition, if mixed subsequently with a propellant. Where the composition comprises both hydrophylic and hydrophobic phases, the weight ratio of the two phases is often in the range of 10:1 to 1:10. Though non-aerosol formulations are favoured in the present invention, aerosol compositions according to the present invention can conveniently be obtained by introducing a base formulation as described herein that is free from propellant and at least 0.7 times and often 1.5 to 20 times its weight of propellant into a suitable aerosol dispenser.

Suitable water-miscible carrier fluids include dihydric alcohols, commonly containing up to 6 carbons, such as propylene glycol, or hexane diol, and/or oligomers of propylene glycol such as dipropylene glycol.

Suitable water-immiscible carriers include volatile and/or non-volatile silicone liquids, volatile and/or non-volatile hydrocarbon liquids, liquid fatty alcohols, liquid esters of fatty alcohols, and liquid ether terminated polyalkylene glycols. Herein liquid indicates that the material has a melting point of not higher than 20° C. Preferably, carrier materials herein have a boiling point of at least 75° C. and particularly in the range of up to 150° C.

Volatile silicones are usually selected from cyclic polysiloxanes containing from 3 to 8 dialkylsiloxane groups, especially dimethylsiloxane groups (cyclomethicones) and particularly 4 and/or advantageously 5 dimethylsiloxane groups (respectively tetra- and/or penta-cyclomethicones). Silicone fluids comprising a minor or major proportion of hexa-cyclomethicone are also useful herein. Other useful volatile silicones can comprise linear polysiloxanes, usually containing up to 8 and preferably 4 or 5 dialkylsiloxane groups, including terminal groups, commonly called dimethicones when both alkyl substituents are methyl. Low molecular weight liquid hydrocarbons that are volatile can comprise paraffin oils, often isoparaffin oils.

Non-volatile silicone oils useful herein usually comprise linear alkylarylpolysiloxanes containing up to 4 or 5 siloxane silicon atoms, such as methylphenylsiloxanes often in which there is from 0.5 to 1.2 phenyl substituent per methyl substituent, as for example in DC704™ available from Dow Corning, Inc. Other non-volatile silicones comprise intermediate and higher molecular weight linear dimethicones that are liquid at 20° C., such as members of the DC200™ series of silicone oils having a viscosity of at least 1 mPa.s, available from Dow Corning, Inc. Non-volatile hydrocarbon oils, which often contain on average between 20 and 40 carbon atoms, include mineral oil and hydrogenated polydecene.

In anhydrous formulations, a significant proportion of the water-immiscible carrier materials can be selected from non-volatile materials such as DC704 and the non-volatile hydrocarbons, at the discretion of the producer, with the intention of reducing the visibility of deposits on topical application of the formulation.

Liquid fatty alcohols are normally branched chain alcohols containing from 12 to 25 carbons and several such desirable alcohols contain from 16 to 20 carbons, including isostearyl alcohol and octyl-decylalcohol.

At the discretion of the producer of the formulation, the respective phases of the composition, be they dispersed particulates in an anhydrous composition, or aqueous and water-immiscible phases, can be refractive indexed matched by selection of the proportions of mixtures of carrier materials and/or treatment of antiperspirant active ingredients, in accordance with published techniques with the intention producing clear or translucent formulations.

Liquid fatty alcohol esters include fatty alcohol esters of naphthoic or especially benzoic acid. In such esters the fatty alcohol is often linear, and in many instances contains from 12 to 20 carbon atoms, such as $C_{12}$–$C_{15}$, or a mixture of chain lengths.

Liquid polyalyleneglycol ethers commonly comprise a polypropyleneglycol polyglycol/polypropylene glycol moiety of from 5 to 20 units terminating in an alkyl ether of from 2 to 6 carbons, such as butyl or t-butyl. A suitable example is obtainable under the CTFA INCI approved name of PPG-14-butyl ether.

In embodiments in which the composition is in the form of an emulsion, it usually contains from 0.1 to 8% by weight of an emulsifier, and in many embodiments from 0.5 to 5%. Materials that are suitable as emulsifiers commonly have an HLB value in the region of from 2 to 10 and often in the region of 3 to 8. In a mixture of emulsifiers, all may have an HLB value in the aforementioned regions or one or more may have a higher HLB value, such as from 10 to 16, provided that the weight averaged HLB value is up to 10 or particularly up to 8. Classes of emulsifiers commonly comprise nonionic surfactants having such an HLB value, including polyalkylene oxide esters or ethers, such as polyethylene oxide (POE) and/or poly propylene oxide (POP) esters or ethers optionally containing a glyceryl unit and/or fatty ester or ether derivatives of a polyhydroxyaliphatic or cycloaliphatic group containing from 3 to 6 carbons, such as glycerol or sorbitol. The number of POE and/or POP units in nonionic surfactant emulsifiers is commonly between 2 and 100 and particularly on weight average between 3 and 25 units and in many instances on average between 4 and 10.

In many non-ionic surfactants desirable as emulsifiers herein, the hydrophobic component therein is usually provided by the alkyl residue of a fatty alcohol or acid, in many instances containing from 12 to 30 carbons, and in particular one or more palmityl, cetyl stearyl and/or eicosonyl or behenyl groups. Of these, stearyl and a mixture of stearyl and cetyl are especially favoured. Another suitable class of emulsifiers, particular interesting when the formulation comprises a significant fraction of a silicone oil, comprises alkyl dimethicone copolymers, namely polyoxyalkylene modified dimethylpolysiloxanes. The polyoxyalkylene group is often a POE or POP or a copolymer of POE and POP. The copolymers often terminate in $C_1$ to $C_{22}$ alkyl groups, particularly $C_{12}$ to $C_{18}$. Suitable example comprises cetyl dimethicone copolymers available as Abil EM90™ or EM97™ from Th.Goldschmidt.

The carrier materials described herein can be thickened, gelled or solidified (structured) employing thickeners, gellants or structurants known to a skilled man in the art for the respective class of carrier materials, and in the amounts needed to achieve the extent of thickening, gelling or structuring desired by the producer. The amount of such thickener, gellant or thickener is usually selected within the range of from 0.1 to 30% by weight of the composition, depending on the nature of the final formulation which the producer wishes to make. Such formulations can comprise liquids of low viscosity, such as from 500 to 5000 mPa.s, which can be employed in roll-on or pump-spray or squeeze-spray dispensers. Other thickened or gelled compositions comprise creams or soft solids, which typically have a hardness of from 0.003 to 0.5 N/mm$^2$, as measured by sphere indentation and frequently, from 0.005 up to 0.1 N/mm$^2$. which compositions flow when subjected to mild pressure (1 to 5 psig) and are commonly dispensed through an apertured dome. Yet other compositions are in the form of sticks which retain their physical integrity and shape when subjected to similar low pressure, usually have a hardness of greater than 0.5 N/mm$^2$, as measured by sphere indentation and are commonly dispensed through the open end of a barrel container.

There are broadly speaking two classes of carrier materials that are employed herein, water and dihydric alcohol in one class and water-immiscible liquids forming a second. The first class can be thickened by water-soluble or dispersible materials of higher viscosity, including various of the emulsifiers, and/or thickened or gelled with water-soluble or water-dispersible polymers including polyacrylates, and water-soluble or dispersible natural polymers, such as water-soluble polysaccharide or starch derivatives, such as alginates, caragheenan, agarose and water-dispersible polymers include cellulose derivatives. An aqueous phase can also be thickened in accordance with known technology using a dispersion of a water-insoluble particulate material, such a finely divided clay, possibly in conjunction with an electrolyte or polyelectrolyte including a water-soluble emulsifier.

Dihydric alcohols, optionally containing ether links such as those described above also can be gelled using dibenzylidene alditols, such as for example dibenzylidene sorbitol.

Water-immiscible carrier fluids, such as those described hereinabove, can be thickened or structured using a wide range of thickeners, gellants and structurants that are known to the skilled producer. Thickeners for such carrier liquids include particulate inorganic substances which are sometimes alternatively referred to as suspending agents particularly if the eventual use of the formulation is in an aerosol, such as clays or finely divided silica. Such thickeners are well suited to increasing the viscosity for liquids, but can also produce semi-solids (soft solids) provided that sufficient thickener is employed.

other materials which can act as thickeners for water-immiscible liquids, but many of which can also act as gellants or structurants by increasing their concentration in the liquid, can comprise organic polymers which are soluble in the carrier liquid(s), though commonly at elevated temperature of above 60° C. Such polymers are particularly well suited to producing compositions in the form of soft or firm solids.

Such polymers can be selected from polysaccharides esterified with a fatty acid of which one excellent example comprises dextrin palmitate: polyamides as discussed in U.S. Pat. No. 5,500,209, such as the product available under the trade name Versamid 950™ that is derived from hexamethylene diamine and adipic acid; alkylene/arylene block copolymers, for example styrene and ethylene, propylene and/or butylene block copolymers eg SEBS block copolymers, many of which are available under the trade name Kraton™: alkyl substituted galactomannan such as N-HANCE™: co-polymers of vinyl pyrrolidone with polyethylene containing at least 25 methylene units. The concentration of such polymers in the water-immiscible liquid is often selected in the range of from 1 to 20%, depending on the extent of thickening or structuring required, and the effectiveness of the chosen polymer in the liquid/mixture.

One class of structurant which is desirable by virtue of its long standing proven capability to produce firm solids and more recently in making soft solids, comprises waxes. Herein, the term wax is employed to encompass not only materials of natural origin that are solid with a waxy feel and water-insoluble at 30–40° C., but melt at a somewhat higher temperature, typically between 50 and 95° C., such as beeswax, candelilla or carnauba wax, but also materials having similar properties. Such other waxes include hydrocarbon waxes, eg paraffin wax, mineral wax and microcrystalline wax; synthetic waxes, such as polyethylene of 2000 to 10000 daltons; waxy derivatives or waxy components of natural waxes, such as ester components, either extracted or synthesised, solid ester derivatives of glyceryl or glycol, typically with linear saturated fatty acids, usually containing a significant fraction of $C_{16-22}$ acid residues, which may be synthesised or obtained by hydrogenating the corresponding natural oil; petroleum waxes, waxy silicone polymers containing alkyl substituents of at least C10 chain length; and, importantly, waxy fatty alcohols, that normally are linear and often contain from 14 to 24 carbons, such as stearyl alcohol, cetyl alcohol and/or behenyl alcohol.

Further classes of structurants for water-immiscible liquids that are employable herein, in accordance with their disclosure in patent literature relating to the preparation of antiperspirant formulations in soft solid or firm stick form include oil-soluble polyamides or amide/silicone copolymers, hydroxystearic acid, such as 12-hydroxystearic acid, or ester or amide derivatives thereof, N-acyl amino acid amides and esters described in U.S. Pat. No. 3,969,087, such as, in particular, N-Lauroyl-L-glutamic acid di-n-butylamide; amide derivatives as set forth in WO 98/27954 notably alkyl N,N'dialkyl succinamides; threitol or like amido gellants as set forth in U.S. Pat. No. 6,410,001; lanosterol, as set forth in U.S. Pat. No. 6,251,377; amido derivatives of cyclohexane as set forth in U.S. Pat. No. 6,410,003; a combination of a sterol and a sterol ester as set forth in WO 00/61096, eg γ-oryzanol and β-sitosterol; and fatty acid esters of cellobiose, such as in particular a product containing predominantly cellobiose octanonanoate and a minor fraction of cellobiose heptanonanoate.

Mixtures of materials within each class of gellant/structurant can be employed, as can mixtures of materials from two or each of the classes.

If the invention composition comprises an aerosol composition, it contains a propellant in addition to a base composition as described herein above, commonly in a weight ratio of from 95:5 to 40:60, and in many formulations, the weight ratio is from 90:10 to 50:50. The propellant is conveniently a low boiling point material, typically boiling below −5° C., for example an alkane such as propane, butane or isobutane, and possibly containing a fraction of pentane or isopentane, or a hydrofluorocarbon or fluorocarbon of similar carbon content. During filling of the aerosol canister, the propellant gas is liquified by virtue of the elevated pressure that is generated therein.

The invention compositions herein can comprise one or more optional constituents which have hither to been incorporated or proposed for incorporation in antiperspirant compositions. Such optional constituents may be liquid or solid, and normally comprise in total not more than 10% by weight of the composition. Such optional constituents can comprise sensory modifiers, such as talc or finely divided polyethylene, such as in an amount of up to 5% by weight; fragrance, including, if desired deoperfumes, often in an amount of up to 4%, eg 0.3 to 2% by weight, colourants; skin cooling agents such as menthol; wash-off agents such as non-ionic surfactants.

The invention compositions can be made by the skilled man using methods known in the antiperspirant industry or described in published literature for the preparation of antiperspirant roll-on, squeeze or pump spray cream or soft solid or firm stick compositions. Likewise, the invention compositions can be dispensed using the appropriate dispensers for such antiperspirant roll-on, squeeze or pump spray cream or soft solid or firm stick compositions as have been employed or described in published literature.

In the second aspect of the present invention, antiperspirant compositions described herein in the first aspect, can be employed in conjunction with a hair removal regime to pre-condition, or ameliorate and/or repair skin damage caused by hair removal, such as irritation and impaired skin condition.

The second aspect of the invention applies to the various methods of hair removal, such as shaving and use of depilators such as mechanical depilators or depilating materials, and is demonstrated especially in regard to wet shaving techniques, ie techniques in which an area of skin from which hair removal is sought is first contacted with water and a shaving composition containing at least one surfactant, commonly a soap or mixture of soaps or other anionic surfactant, and usually with various other constituents, and thereafter a sharp blade or series of blades, usually retained in a holder, is pressed against and passed across the skin surface to cut through hair follicles close to their base.

Mechanical depilators commonly trap hair follicles within coils of a spring or in slits of a flexible strip that are first opened to permit follicle entry and then closed to trap the follicle, as part of a cycle in which the coil spring or strip slit is brought towards the skin/follicles, often by rotation or flexing, the follicle is trapped and the spring or strip slit is closed and moved away from the skin surface. The cycle is commonly repeated frequently during depilation. Materials for depilation include waxes which are applied when still molten, allowed to solidify on the skin trapping hair follicles and the entire mass of wax and follicles is ripped off. The waxy material may be applied via a blade or attached to a backing strip, preferably having a wax-free tab to assist the material to be ripped away.

Most people, normally females, who remove hair from their axillae, do so either regularly or for special occasions. If they do so regularly, then it is important that a cosmetic antiperspirant continues to enable the skin to resist the repeated challenges from shaving or other methods of hair removal. On the other hand, if the user depilates only intermittently, then its localised impact on the skin tends to be greater. Thus, it is particularly important that the antiperspirant formulation aids recovery.

In accordance with this second aspect, in some regimes, users employ a cycle in which:
i) an antiperspirant composition is applied to skin in a chosen region of the body, and in particular an axilla,
ii) is left in place whilst the user carries out her desired activities, controlling the local appearance of sweat on the skin,
iii) optionally said skin is washed
iv) a shaving composition is applied to said skin and a sharp blade is pressed at an acute angle against and passed across said skin
v) optionally, the skin is rinsed and dried and
vi) steps i) and ii) are repeated.

For persons who remove hair regularly, steps i) and ii) often occur from 1 to 14 times and particularly from 1 to 7 times, between each occurrence of step iv). Commonly antiperspirant formulation is applied at least once a day, sometimes twice, and less commonly 3 or 4 times. Hair removal, for example by shaving, is carried out weekly by many, two or three times a week by others and daily or most days by some.

Step vi) often takes place shortly after step iv, for example within 30 minutes and in many instances within 10 minutes. It is an advantage of the instant antiperspirant formulations which contain the combination of both glycerol and glyceride oils that they can be used so soon after shaving, and that by so doing they can start to counter the irritation and other detrimental skin effects prompted by shaving.

In a further aspect of the invention, there is provided a first kit of parts, comprising a) a shaving composition comprising at least one soap and alternatively or additionally another anionic surfactant salt, for use in conjunction with a razor and b) an antiperspirant composition according to the first aspect. The kit may further comprise instructions, either on the respective containers of the compositions or on a container for the kit or an instruction leaflet incorporated therewith or affixed thereto, on how to use the shaving composition and the antiperspirant composition, though in practice, such use instructions may be assumed by the intended user in view of their expected previous practice in shaving and applying antiperspirant. In a second kit of parts, the constituents of the first kit are supplemented by a razor.

Although the second aspect of the present invention has been described herein above with respect to hair removal by shaving, a corresponding cycle arises when a mechanical depilator is or depilation materials are employed. A further kit of parts according to the invention comprises an antiperspirant formulation according to the first aspect herein and a mechanical depilator or depilating materials.

Selected embodiments of the present invention will now be described more fully by way of example only.

The Examples hereinbelow employ as a representative natural glyceride oil, sunflower oil. Invention compositions can be made similarly by substituting the same weights of maize corn oil, evening primrose oil, coriander seed oil, safflower oil or borage seed oil therefor.

EXAMPLES 1 to 3

In these Examples, the benefits of employing an antiperspirant composition in accordance with the present invention together with a hair-removal regime are demonstrated using representative roll-on formulations which comprised:

TABLE 1

| Constituent | % by weight |
|---|---|
| aluminium chlorohydrate in 50% w/w aqueous solution | 17.5 |
| POE steareth emulsifier (mixture of from 2 to 100 POE units, average ~5.4) | 3.2 |
| Glycerol | 4.0 |
| Sunflower oil (weight ratio of oleic to linoleic residue of ~2:1) | 4.0 |
| Fragrance | 1.0 |
| Water (total) | 70.3 |

TABLE 2

| Constituent | % by weight |
|---|---|
| aluminium chlorohydrate in 50% w/w aqueous solution | 17.5 |
| Ceteareth 20 | 3.0 |
| Cetyl alcohol/Glyceryl stearate/decyl oleate | 5.0 |
| Fragrance | 1.2 |
| Water (total) | 73.3 |

The compositions described in Tables 1 and 2 were made by a conventional method known in the art for making an aqueous roll-on formulation.

In Example 1, a panel of 30 healthy female volunteers aged between 18 and 55 was recruited carried out the following protocol in 2002 in England:

In the first week, the volunteers shaved their underarms once a day using a Wilkinson Sword Extra Precision™ disposable razor, the skin having been moistened with a topical application of a Lux™ soap bar. Antiperspirant was applied topically, firstly shortly after shaving was completed and the armpits rinsed, and on a further 3 times at intervals during the day, using a composition not according to the present invention, Secret Clear Dry Stick™.

During the following four weeks, panellists shaved their armpits in the same way, but twice a week and applied a test antiperspirant roll-on solution in Table 1 or a comparative antiperspirant roll-on solution in Table 2 to respectively either the left or the right armpit four times daily, at regular intervals, half applying the test solution to the left armpit and half to the right. The panellists avoided washing their armpits for 2 hours after applying the antiperspirant, and did not employ any other washing product on the underarms during the test.

During the test period, panellists were visually assessed on Mondays, Wednesdays and Fridays by a trained, expert assessor. In addition, the panellists kept a diary to record any incidents of itch, sting, burn or any other irritable under-arm sensation that they perceived, either on application of the antiperspirant composition or subsequently and at the end of the test completed a questionnaire. Various sensory criteria were assessed in that way, to indicate whether the skin was perceived to be soft, smooth, comfortable or healthy, using a 5 point scale, in which 1 was best and 5 was worst.

| Positive attributes | | Negative attributes |
|---|---|---|
| extremely | 1 | not at all |
| very | 2 | slightly |
| moderately | 3 | moderately |
| slightly | 4 | very |
| not at all | 5 | extremely |

The benefits of the invention composition can be seen from the data below:

TABLE 3

Cumulative score of visible occurrences of visible irritation

| | Score | |
|---|---|---|
| Days into test | Invention | Comparison |
| 5 | 3 | 4 |
| 8 | 4 | 5 |
| 12 | 5 | 7 |
| 15 | 5.5 | 8 |
| 19 | 6 | 9.5 |
| 22 | 7 | 11 |
| 26 | 8 | 13 |
| 30 | 8 | 14 |

From Table 3, it can be seen that the invention composition provoked significantly fewer occurrences of visible irritation demonstrating that it was kinder to the skin in a shaving regime that is employed by a substantial fraction of persons who remove hair from their armpits.

From their self-assessments, the panellists indicated that use of the invention composition was consistently superior to the comparison composition on the positive or negative attributes recorded, including, soft, smooth, supple, comfortable, healthy, irritated and sore, for the skin within the range of 0.25 to 0.4, in each case at a confidence level of greater than 95%. Thus confirms the value of employing the invention composition in combination with a shaving regime compared with the comparison antiperspirant.

The panellists also provided data to assess whether the compositions on applications stung the user. The cumulative number of events recorded were summed for each composition. After 29 days, the comparative score for the comparative composition was just over 1.5, whereas the score for the invention composition was only 0.4, which is over 3 times better and indicates significantly less stinging.

EXAMPLE 2

In this Example, the test was repeated, but in the week before the comparative test, the user employed the same comparative roll-on composition as in the test period. This second comparison was a differently fragranced variant of the comparison roll-on composition used in Example 1. The invention composition in this Example was the same as that in Example 1, except for using nominally the same emulsifier system from a different supplier. Similar results to the results shown above were obtained, but in addition, the trained assessor also measured during the Monday, Wednesday, Friday assessments, the extent of hydration of the stratum corneum in a conventional manner using a Corneometer CM825™ available from Courage & Khazaka Electronic GmbH. The difference in hydration of approximately 0.2 in 3.1/3.3 was statistically significant at the 95% confidence limit, in favour of the invention composition. This confirms that the invention composition was repairing the stratum corneum faster than the comparison composition.

EXAMPLE 3

In this Example, the tests were repeated employing the invention composition of Example 2 and as a comparison a competitor's commercial roll-on product analysing Water, aluminium chlorohydrate; PPG-15 stearyl ether; Steareth 2; Steareth-21; Parfum; PEG-8; Trisodium-EDTA; Glyceryl laurate; Persae Gratissima; Citric acid; Octyl dodecanol.

The invention composition recorded a lower visible irritation score which became significant from about day 8 till the end of the study on day 29. Since the application of antiperspirant is often daily and periodic armpit hair removal are activities which are continued for many years, data obtained at the end of the study is especially pertinent compared with data on the first few days of the study. In the self-assessment tests, the invention product was superior to that of the comparison in all the attributes, and statistically significant at the 95% confidence limit or better for softness, comfort, and irritation.

EXAMPLE 4

A representative pump spray composition.

TABLE 4

| Constituent | % by weight |
| --- | --- |
| Al-Zr Pentachloro-hydrate (40%) | 50.00 |
| Distilled Water | 31.45 |
| Cyclomethicone D5 | 4.0 |
| Glycerol | 4.0 |
| Sunflower Oil | 4.0 |
| Glyceryl Stearate, Ceteareth-20, Ceteareth-12, Cetearyl Alcohol, Cetyl Palmitate | 2.0 |
| Amphoteric Potato Starch | 1.0 |
| Perfume | 1.0 |
| Glyceryl stearate | 1.0 |
| Cetearyl Alcohol, PEG 20 Stearate | 0.65 |
| Ceteareth 20 | 0.4 |
| Octyldodecanol | 0.5 |

EXAMPLE 5

This Example describes a representative stick composition.

TABLE 5

| Constituent | % by weight |
| --- | --- |
| Cyclomethicone D5 | 36.5 |
| AZAG* | 24.0 |
| non-volatile silicone 10 mPa · s | 7.5 |
| PPG-14 butyl ether | 6.0 |
| Stearyl alcohol | 14.5 |
| polyethylene powder | 3.0 |

TABLE 5-continued

| Constituent | % by weight |
| --- | --- |
| Castor wax | 2.0 |
| Talc | 2.0 |
| Glycerol* | 2.0 |
| Sunflower oil | 1.0 |
| Fragrance | 0.8 |
| Steareth 100 | 0.7 |

Ingredients marked * in these Examples were combined in a prior preparative stage before the remainder of the constituents were brought together.

EXAMPLE 6

Representative aerosol formulation

TABLE 5

| Constituent of base composition | % by weight |
| --- | --- |
| Particulate Activated aluminium chlorohydrate* | 39.0 |
| cyclomethicone D5 | 20.8 |
| PPG-14 butyl ether | 22.8 |
| Fragrance | 5.4 |
| Hydrophobic clay | 4.2 |
| Sunflower oil | 4.0 |
| Glycerol* | 2.0 |
| Octyldocecanol | 1.0 |
| Dimethicone copolyol | 0.8 |

To make the final aerosol composition, 1 part by weight of base composition was introduced into an aerosol canister followed by 3 parts by weight of a propellant comprising a mixture of propane, butane and isobutane.

EXAMPLE 7

Representative Soft Solid Formulation

TABLE 6

| Constituent | % by weight |
| --- | --- |
| cyclomethicone D5 | 40.7 |
| Particulate AZAG* | 24.5 |
| PPG-14 butyl ether | 10.5 |
| Castor wax | 6.0 |
| low melting point wax (eg stearyl alcohol) | 6.0 |
| Talc | 6.0 |
| Sunflower oil | 2.0 |
| Glycerol* | 2.0 |
| Silica | 1.5 |
| Fragrance | 0.8 |

EXAMPLE 8

Representative gel composition

TABLE 7

| Constituent | % by weight |
| --- | --- |
| Propylene glycol | 45.5 |
| Al-Zr chlorohydrate glycine complex | 25.0 |
| Dipropylene glycol | 11.0 |
| Isostearyl alcohol | 11.0 |
| Dibenzoyl sorbitol | 3.0 |
| Glycerol | 2.0 |

TABLE 7-continued

| Constituent | % by weight |
|---|---|
| Sunflower oil | 2.0 |
| 3-amino-1-propanol | 0.5 |

EXAMPLE 9

In this Example, the skin hydrating effect of different proportions of the sunflower oil and the glycerol on shaven skin was demonstrated compared with not adding either, employing variations of the roll-on compositions of Example 1 made in the same way. The variations and the overall extent of hydration of the skin as measured by the Corneometer CM825™ are summarised in Table 8 below. Variations 9.1, 9.2 and 9.3 are in accordance with the invention whereas variation 9.A is not.

TABLE 8

| | Comparison/Examples | | | |
|---|---|---|---|---|
| Constituent | 9.A | 9.1 | 9.2 | 9.3 |
| | parts by weight | | | |
| Base | | | | |
| aluminium chlorohydrate | | 17.5 | | |
| POE steareth emulsifier | | 3.2 | | |
| Fragrance | | 1.0 | | |
| Water | | 70.3 | | |
| Addition | | | | |
| Sunflower oil | 0 | 1 | 4 | 4 |
| glycerol | 0 | 4 | 2 | 4 |
| water | 8 | 3 | 2 | 0 |
| Skin hydration by Corneometer | 27.9 | 30.1 | 28.6 | 30.6 |

From Table 8, it can be seen that the addition of both the sunflower oil and the glycerol resulted in an increase in skin hydration and that the best result was obtained by addition of 4% of each of the two constituents and the second best result was obtained with 4% glycerol and 2% sunflower oil.

Skin Hydration in this Example was measured on the volar forearm of volunteer panellists who were requested in the period of 3 weeks before the study to avoid the excessive use shower gel, soap or similar cleansing agents on the forearm, applying body creams or moisturisers to the forearm and to avoid any other test studies on the test sites. Each volunteer had two sites, each of 20 cm$^2$ area, marked on the forearm with indelible ink, so that each variation was tested on 12 sites.

On the Monday of the study, each site was shaven by an operator (not the volunteer) without either water or a shaving product, using a disposable razor. Approximately 5 hours later the hydration of the skin was measured using the aforementioned Corneometer to establish a baseline against which any hydration change could be compared. After the baseline measurement had been made, the volunteers applied an aliquot of 0.2 g of a coded product to a site. On the following Tuesday to Friday mornings, a further aliquot of 0.2 g of the same product was applied to that site and 5 hours later, the hydration level of the stratum corneum was measured using the same Corneometer set up with the same parameters. From the results over the last 4 days, an averaged overall hydration for each site was determined.

The procedure was repeated on 3 further weeks using different panels.

We claim:

1. An antiperspirant or deodorant composition suitable for topical application to skin and providing a skin-care benefit which comprises:
   a) an antiperspirant active in an amount of from 1 to 50 by weight,
   b) a natural oil that comprises a glyceride of an unsaturated carboxylic acid containing 18 carbon atoms
   c) glycerol constituents b) and c) being selected in a weight ratio of from 4:1 to 1:4 and together constituting 1.5 to 15% by weight of the composition and
   d) a carrier fluid for the antiperspirant active other than constituents b) and c) which is free from a low molecular weight aliphatic monohydric alcohol in an amount of from 30 to 93% by weight.

2. A composition according to claim 1 in which the glyceride in the natural oil comprises a carboxylic acid residue from a unsaturated carboxylic acid containing 1, 2 or 3 olefinic bonds.

3. A composition according to claim 2 in which the carboxylic acid residue is derived from oleic, linoleic, linolenic or recinoleic acid.

4. A composition according to claim 2 in which the carboxylic acid residue is derived from petroselinic acid, 7-octadecenoic acid, parinaric acid, pinolenic acid, punicic acid and stearidonic acid.

5. A composition according to claim 2 in which the natural oil comprises at least one oil selected from coriander seed oil, borage seed oil, evening primrose oil, maize corn oil, sunflower oil and safflower oil.

6. A composition according to claim 5 in which the natural oil comprises sunflower oil.

7. A composition according to claim 6 in which the sunflower oil contains rich in oleic acid residues compared with linoleic acid residues.

8. A composition according to claim 6 in which the sunflower oil contains rich in linoleic acid residues compared with oleic acid residues.

9. A composition according to claim 1 in which the weight proportion of glyceride-containing natural oil is in the range of 0.3 to 10%, in the composition excluding any propellant.

10. A composition according to claim 9 in which the weight proportion of glyceride-containing natural oil is in the range of 0.5 to 6%, in the composition excluding any propellant.

11. A composition according to claim 1 in which the weight proportion of glycerol in the composition, excluding any propellant, is from 0.5 to 10%.

12. A composition according to claim 11 in which the weight proportion of glycerol in the composition, excluding any propellant, is from 0.5 to 6%.

13. A composition according to claim 1 in which the combined weight of glycerol and glyceride-containing natural oil is from 2 to 8%, in the composition excluding any propellant.

14. A composition according to claim 1 in which the weight ratio of the natural oil to the glycerol is at least 1:1.

15. A composition according to claim 14 in which the weight ratio of natural oil to glycerol is no greater than 2:1.

16. A composition according to claim 1 in which the antiperspirant active salt is present at a concentration of from 15 to 30% by weight in a composition that is free from propellant.

17. A composition according to claim 1 in which the antiperspirant active salt is selected from aluminium chlorohydrate and activated aluminium chlorohydrate at a concentration of from 10 to 50% in a base composition intended for mixture with apropellant.

18. A composition according to claim 1 in which the carrier fluid comprises water.

19. A composition according to claim 1 in which the water comprises from 50 to 75% by weight of the composition.

20. A composition according to claim 18 employing an aqueous solution of aluminium chlorohydrate, zirconium aluminium chlorohydrate or zirconium aluminium chlorohydrate glycine complex.

21. A composition according to claim 18 in which the water or aqueous solution is thickened with a non-ionic surfactant.

22. A composition according to claim 1 in which the carrier liquid comprises a water-immiscible oil as a continuous phase.

23. A composition according to claim 22 in which the water-immiscible oil comprises a volatile silicone oil and optionally contains one or more non-volatile oils selected non-volatile silicone oils, polyalkylene glycol ethers and alkyl benzoate esters.

24. A composition according to claim 22 in which the water-immiscible oil phase is present in an amount of from 30 to 65% by weight.

25. A composition according to claim 22 in which the water-immiscible phase is thickened with a particulate inorganic thickener in an amount of from 0.5 to 4% by weight.

26. A composition according to claim 22 in which the water-immiscible phase is thickened or solidified with an organic geilant or structurant in an amount of from 1 to 30% by weight.

27. A composition according to claim 26 in which the organic gellant or structurant is selected from waxes.

28. A composition according to claim 27 in which the wax comprises a fatty alcohol.

29. A composition according to claim 1 in which the carrier comprises propylene glycol and/or dipropylene glycol.

30. A composition according to claim 29 in which the carrier is gelled by dibenzylidene sorbitol.

* * * * *